US012595224B2

(12) United States Patent
Kim et al.

(10) Patent No.: US 12,595,224 B2
(45) Date of Patent: Apr. 7, 2026

(54) METHOD FOR PRODUCING ACRYLIC ACID

(71) Applicant: LG CHEM, LTD., Seoul (KR)

(72) Inventors: Mi Kyung Kim, Daejeon (KR); Hyebin Kim, Daejeon (KR); Jaeik Lee, Daejeon (KR); Eunkyo Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 593 days.

(21) Appl. No.: 17/920,861

(22) PCT Filed: Oct. 27, 2021

(86) PCT No.: PCT/KR2021/015177
§ 371 (c)(1),
(2) Date: Oct. 24, 2022

(87) PCT Pub. No.: WO2022/119127
PCT Pub. Date: Jun. 9, 2022

(65) Prior Publication Data
US 2023/0131529 A1     Apr. 27, 2023

(30) Foreign Application Priority Data

Dec. 3, 2020     (KR) ........................ 10-2020-0167556

(51) Int. Cl.
*C07C 51/377*     (2006.01)
*C07C 51/44*     (2006.01)
(52) U.S. Cl.
CPC ............ *C07C 51/377* (2013.01); *C07C 51/44* (2013.01)

(58) Field of Classification Search
CPC ..... C07C 51/377; C07C 51/44; C07C 51/487; C07C 57/04; Y02P 20/10
USPC ........................................................ 562/599
See application file for complete search history.

(56) References Cited

U.S. PATENT DOCUMENTS

| | | | |
|---|---|---|---|
| 7,632,968 B2 | 12/2009 | Kang et al. | |
| 9,745,244 B2 | 8/2017 | Ligon et al. | |
| 9,783,479 B1 | 10/2017 | Jain et al. | |
| 10,239,816 B2 | 3/2019 | Jain et al. | |
| 10,308,582 B2 | 6/2019 | Binder et al. | |

(Continued)

FOREIGN PATENT DOCUMENTS

| | | | |
|---|---|---|---|
| CN | 101255109 | | 9/2008 |
| CN | 101255109 A | * | 9/2008 |

(Continued)

*Primary Examiner* — Fereydoun G Sajjadi
*Assistant Examiner* — Y. Lynnette Kelly-O'Neill
(74) *Attorney, Agent, or Firm* — Bryan Cave Leighton Paisner LLP

(57)     ABSTRACT

Provided is a method for producing acrylic acid, the method including: preparing a reaction product containing acrylic acid by supplying lactic acid to a reactor and performing a dehydration reaction; supplying a reactor discharge stream containing the reaction product to a cooling tower and condensing the result to transfer a lower discharge stream including a condensate to an acrylic acid purification unit and supplying a non-condensate discharged as an upper discharge stream to a distillation tower; and, in the distillation tower, circulating the lower discharge stream containing acrylic acid to the cooling tower, and removing acetaldehyde from the upper discharge stream.

6 Claims, 2 Drawing Sheets

(56)          References Cited

U.S. PATENT DOCUMENTS

| | | | | |
|---|---|---|---|---|
| 2009/0253934 A1* | 10/2009 | Ho | ........................... | C07C 51/44 |
| | | | | 562/600 |
| 2009/0299095 A1* | 12/2009 | Briegel | ................... | C07C 51/42 |
| | | | | 562/600 |
| 2010/0113822 A1 | 5/2010 | Craciun et al. | | |
| 2011/0036704 A1* | 2/2011 | Blum | .................... | C07C 51/252 |
| | | | | 203/31 |
| 2014/0105792 A1* | 4/2014 | Baek | ...................... | C07C 51/44 |
| | | | | 422/187 |
| 2015/0329462 A1* | 11/2015 | Godlewski | .............. | C07C 51/47 |
| | | | | 562/598 |

FOREIGN PATENT DOCUMENTS

| | | |
|---|---|---|
| CN | 101260035 A | 9/2008 |
| JP | 2014-189510 | 10/2014 |
| JP | 2014-189513 | 10/2014 |
| KR | 10-2006-0048785 | 5/2006 |
| KR | 10-1662093 | 10/2016 |
| KR | 10-2017-0088963 | 8/2017 |
| KR | 10-2017-0113177 | 10/2017 |
| KR | 10-2017-0128262 | 11/2017 |
| WO | 2005-095320 | 10/2005 |

\* cited by examiner

【FIG. 1】
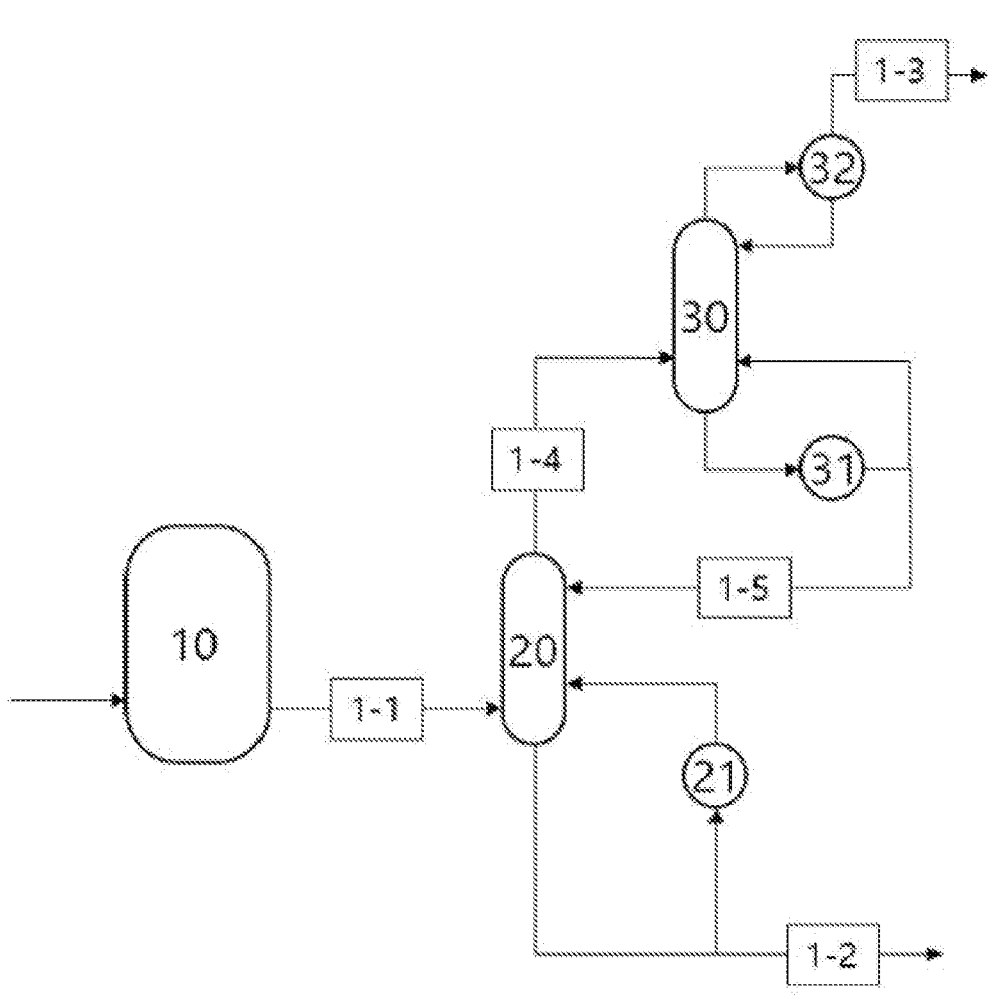

【FIG. 2】
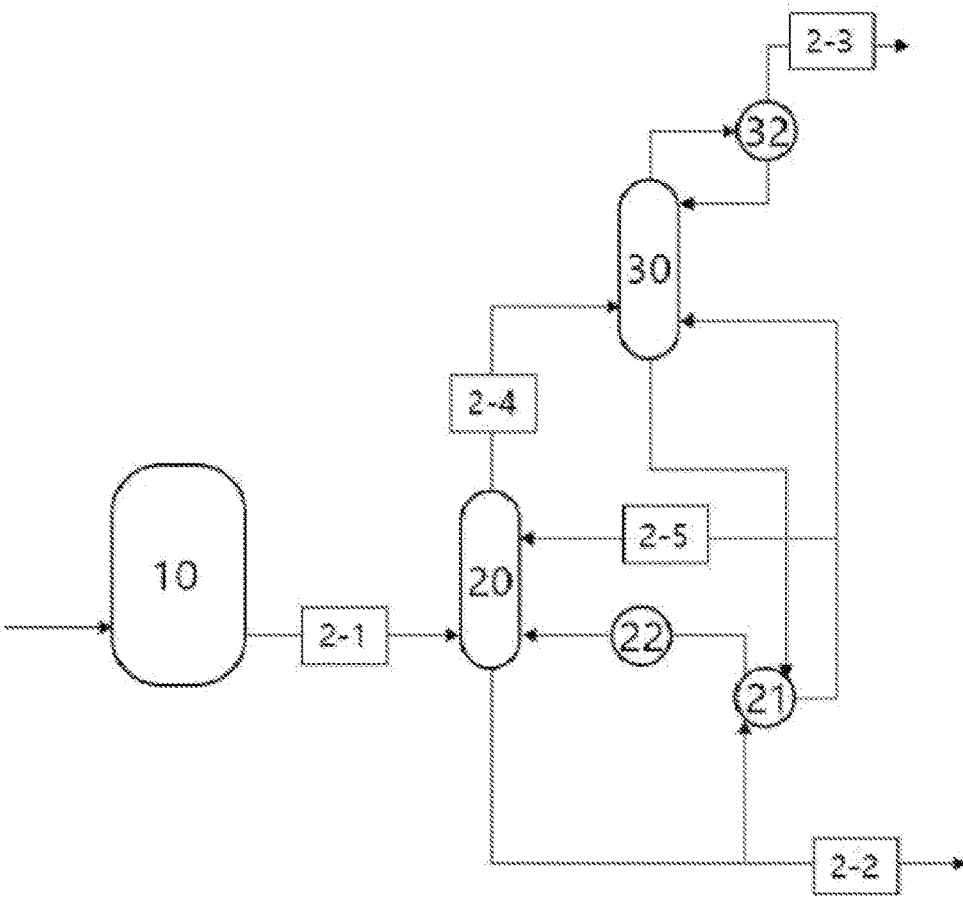
【FIG. 3】
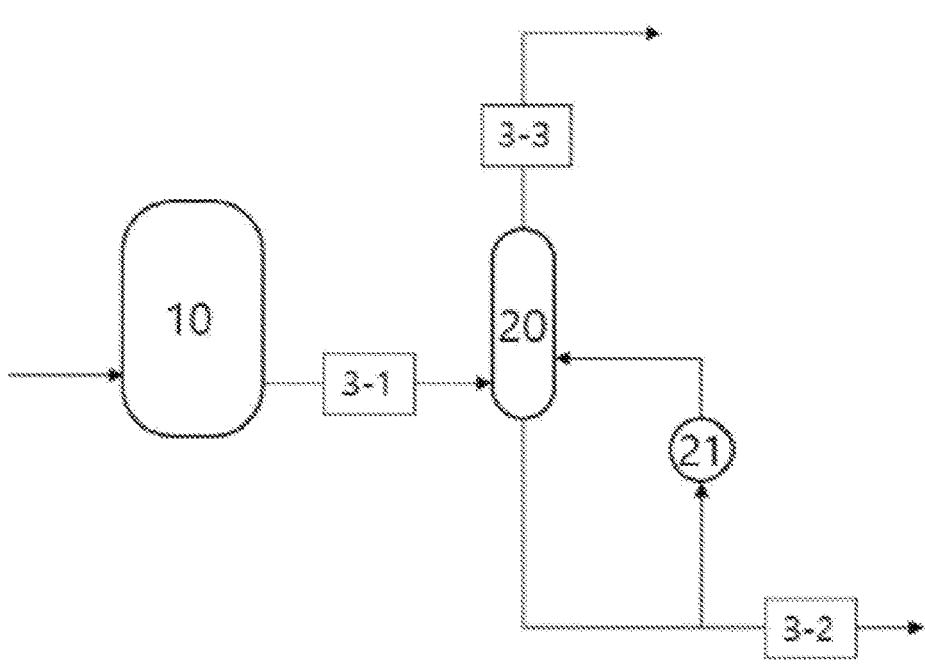

METHOD FOR PRODUCING ACRYLIC ACID

CROSS-REFERENCE TO RELATED APPLICATION(S)

This application is a National Stage Application of International Application No. PCT/KR2021/015177 filed on Oct. 27, 2021, which claims priority to and the benefits of Korean Patent Application No. 10-2020-0167556, filed with the Korean Intellectual Property Office on Dec. 3, 2020, the entire contents of which are incorporated herein by reference.

TECHNICAL FIELD

The present disclosure relates to a method for producing acrylic acid, and in particular, to a method of, in producing acrylic acid through a dehydration reaction of lactic acid, preventing loss of acrylic acid while effectively removing acetaldehyde produced as a by-product.

BACKGROUND

Acrylic acid is used as a polymer raw material used in fibers, adhesives, paints, fiber processing, leather, construction materials and the like, and demands thereon are expanding. In addition, the acrylic acid is also used as a raw material of absorbent polymers, and is widely used industrially in applications such as absorbent materials such as paper diapers and sanitary napkins, water-retaining agents for agriculture and horticultural uses, and waterstops for industrial uses.

An existing method for producing acrylic acid generally uses a method of air oxidizing propylene, however, this method is a method of converting propylene to acrolein using a gas-phase catalytic oxidation reaction, and gas-phase catalytic oxidation reacting the result to prepare acrylic acid, and the method produces acetic acid as a by-product, which is difficult to separate from the acrylic acid. In addition, the method for producing acrylic acid using propylene employs propylene obtained by refining crude oil, a fossil resource, and has problems in terms of raw material costs or environmental pollution considering problems such as recent rises in crude oil prices or global warming.

In view of the above, studies on a method for producing acrylic acid from a carbon-neutral biomass raw material have been conducted. For example, a method for producing acrylic acid (AA) through a gas-phase dehydration reaction of lactic acid (LA) can be included. This method is a method of producing acrylic acid through an intramolecular dehydration reaction of lactic acid generally at a high temperature of 300° C. or higher and under the presence of a catalyst. However, during the dehydration reaction of lactic acid, a side reaction other than the dehydration reaction occurs, which produces, as a reaction product, acetaldehyde (ACHO) as a by-product in addition to the acrylic acid. This has a problem in that quality and productivity of a product decline by facilitating polymer formation in the acrylic acid purification process caused by acetaldehyde, the by-product produced through the dehydration reaction of lactic acid.

PRIOR ART DOCUMENTS (Patent Document 1) JP 2014-189513 A

BRIEF DESCRIPTION

Technical Problem

The present disclosure has been made in view of the problems mentioned in the background, and is directed to providing a method of, in producing acrylic acid through a dehydration reaction of lactic acid, effectively removing acetaldehyde that is a by-product, and minimizing the amount of acrylic acid lost during this process.

Technical Solution

One embodiment of the present disclosure provides a method for producing acrylic acid, the method including preparing a reaction product including acrylic acid by supplying lactic acid to a reactor and going through a dehydration reaction; supplying a reactor discharge stream including the reaction product to a cooling tower and condensing the result to transfer a lower discharge stream including a condensate to an acrylic acid purification unit and supply a non-condensate discharged as an upper discharge stream to a distillation tower; and, in the distillation tower, circulating a lower discharge stream including acrylic acid to the cooling tower, and removing acetaldehyde from an upper discharge stream.

Advantageous Effects

According to a method for producing acrylic acid of the present disclosure, a reaction product including acrylic acid is condensed in a cooling tower, and by operating the cooling tower so as to minimize an amount of acetaldehyde effused to the lower portion, the amount of acetaldehyde transferred to an acrylic acid purification unit can be reduced. Through this, quality and productivity of a product can be enhanced by preventing polymer formation in the acrylic acid purification process caused by acetaldehyde.

In addition, in order to operate the cooling tower so as to minimize the amount of acetaldehyde effused to the lower portion, a certain amount of water is effused to an upper portion of the cooling tower, and herein, loss of acrylic acid occurs, and in regard thereto, the present disclosure is capable of preventing the loss of acrylic acid by placing a distillation tower above the cooling tower, recovering acrylic acid to a lower portion of the distillation tower, and circulating the acrylic acid back to the cooling tower.

In addition, by controlling operation conditions of the cooling tower and the distillation tower in the present disclosure, acrylic acid can be recovered without increasing the amount of process energy used by utilizing heat removed from a cooler below the cooling tower as a heat source required for a reboiler below the distillation tower.

DESCRIPTION OF THE DRAWINGS

FIG. 1 and FIG. 2 are each a process flow chart according to a method for producing acrylic acid in one embodiment of the present disclosure.

FIG. 3 is a process flow chart according to a method for producing acrylic acid in a comparative example.

REFERENCE NUMERALS

10: Reactor
20: Cooling Tower

21: First Cooler
22: Second Cooler
30: Distillation Tower
31: Reboiler
32: Condenser

DETAILED DESCRIPTION

Terms or words used in the descriptions and the claims of the present disclosure are not to be interpreted limitedly to common or dictionary meanings, and shall be interpreted as meanings and concepts corresponding to technical ideas of the present disclosure based on a principle in which the inventors can suitably define the concepts of terms in order to describe the invention in the best possible way.

In the present disclosure, a term "upper portion" can mean a portion corresponding to a height of 50% or greater from the total height of a container or a device, and a term "lower portion" can mean a portion corresponding to a height of less than 50% from the total height of a container or a device.

In the present disclosure, a term "stream" can mean a flow of a fluid in a process, or can mean a fluid itself flowing in a pipe. Specifically, the stream can mean a fluid itself flowing in a pipe connecting each device and a flow of the fluid at the same time. In addition, the fluid can mean a gas, a liquid or the like. A case of the fluid including a solid component is not excluded.

Hereinafter, the present disclosure will be described in more detail with reference to FIG. 1 and FIG. 2 in order to illuminate the present disclosure.

One embodiment of the present disclosure provides a method for producing acrylic acid. More specifically, the method can include preparing a reaction product including acrylic acid by supplying lactic acid to a reactor (10) and going through a dehydration reaction; supplying a reactor (10) discharge stream including the reaction product to a cooling tower (20) and condensing the result to transfer a lower discharge stream including a condensate to an acrylic acid purification unit, and supply a non-condensate discharged as an upper discharge stream to a distillation tower (30); and, in the distillation tower (30), circulating a lower discharge stream including acrylic acid to the cooling tower (20), and removing acetaldehyde from an upper discharge stream.

Specifically, an existing method for producing acrylic acid generally uses a method of air oxidizing propylene, however, this method is a method of converting propylene to acrolein using a gas-phase catalytic oxidation reaction, and gas-phase catalytic oxidation reacting the result to prepare acrylic acid, and the method produces acetic acid as a by-product, which is difficult to separate from the acrylic acid. In addition, the method for producing acrylic acid using propylene employs propylene obtained by refining crude oil, a fossil resource, and has problems in terms of raw material costs or environmental pollution considering problems such as recent rises in crude oil prices or global warming.

In order to resolve problems of the existing method for producing acrylic acid, studies on a method for producing acrylic acid from a carbon-neutral biomass raw material have been conducted. For example, a method for producing acrylic acid (AA) through a gas-phase dehydration reaction of lactic acid (LA) can be included. This method is a method of producing acrylic acid through an intramolecular dehydration reaction of lactic acid generally at a high temperature and under the presence of a catalyst. However, during the dehydration reaction of lactic acid, a side reaction other than the dehydration reaction occurs, which produces, as a reaction product, acetaldehyde (ACHO) as a by-product in addition to the acrylic acid. This has a problem in that quality and productivity of a product decline by facilitating polymer formation in the acrylic acid purification process caused by acetaldehyde, the by-product produced through the dehydration reaction of lactic acid. Accordingly, studies on separating acetaldehyde before purifying acrylic acid have been conducted, and herein water needs to be effused to an upper portion of a cooling tower (20) in order to effectively separate acetaldehyde, and there has been a problem of losing acrylic acid during this process.

In view of the above, the present disclosure is directed to providing a method for producing acrylic acid capable of, while producing acrylic acid through a dehydration reaction of lactic acid, effectively removing acetaldehyde produced as a by-product in the manufacturing process, and enhancing quality and productivity of a product as well by preventing loss of acrylic acid.

According to one embodiment of the present disclosure, a reaction product including acrylic acid can be prepared by supplying lactic acid to a reactor (10) and going through a dehydration reaction. Herein, the lactic acid can be introduced to the reactor (10) in an aqueous solution state, or the dehydration reaction can be conducted in a gas-phase reaction under the presence of a catalyst. For example, the lactic acid can be introduced to the reactor (10) as an aqueous lactic acid solution including lactic acid in 10% by mass to 90% by mass or 20% by mass to 80% by mass.

The reactor (10) can be a reactor capable of conducting a common dehydration reaction of lactic acid, and examples thereof can include a stirring-type reactor, a fixed-bed reactor, a fluidized bed reactor and the like. In addition, the reactor (10) can include a reaction pipe filled with a catalyst, and, while passing a reaction gas including a volatile component of the aqueous lactic acid solution, a raw material, through the reaction pipe, lactic acid is dehydrated using a gas-phase catalytic reaction to produce acrylic acid. The reaction gas can further include, in addition to lactic acid, any one or more dilution gases of water vapor, nitrogen and air for a concentration adjustment.

As for an operation condition of the reactor (10), the reactor can be operated under a common dehydration reaction condition of lactic acid, and for example, the temperature can be from 250° C. to 500° C., 250° C. to 450° C. or 300° C. to 400° C. Herein, the operation temperature of the reactor (10) can mean a setting temperature of a heat medium or the like used for controlling the temperature of the reactor (10). In addition, the reactor (10) can have an operation pressure of 30 kPa to 1000 kPa, 50 kPa to 500 kPa or 60 kPa to 300 kPa.

Examples of the catalyst used in the dehydration reaction of lactic acid can include one or more types selected from the group consisting of sulfate-based catalysts, phosphate-based catalysts and nitrate-based catalysts. As a specific example, the sulfate can include $Na_2SO_4$, $K_2SO_4$, $CaSO_4$ and $Al_2(SO_4)_3$, the phosphate can include $Na_3PO_4$, $Na_2HPO_4$, $NaH_2PO_4$, $K_3PO_4$, $K_2HPO_4$, $KH_2PO_4$, $CaHPO_4$, $Ca_3(PO_4)_2$, $AlPO_4$, $CaH_2P_2O_7$ and $Ca_2P_2O_7$, and the nitrate can include $NaNO_3$, $KNO_3$ and $Ca(NO_3)_2$. In addition, the catalyst can be supported on a support. Examples of the support can include one or more types selected from the group consisting of diatomite, alumina, silica, titanium dioxide, carbide and zeolite.

The reaction product produced through the dehydration reaction of lactic acid can further include, in addition to acrylic acid that is a target product, a by-product such as water ($H_2O$), acetaldehyde (ACHO), carbon monoxide (CO), carbon dioxide ($CO_2$), a dilution gas and a high-boiling-point material. Herein, the content of acetaldehyde included in the reaction product can be approximately from 5% to 60% with respect to the content of acrylic acid. Accordingly, a purifying process is required for separating acrylic acid from the reaction product.

According to one embodiment of the present disclosure, the reactor (10) discharge stream including the reaction product can be supplied to the cooling tower (20) for cooling before transferring to the acrylic acid purification unit. Specifically, the reactor (10) discharge stream including the reaction product can be supplied to the cooling tower (20) and condensed through cooling since it is discharged in a gas phase. A condensate condensed in this process is transferred to the acrylic acid purification unit as a cooling tower (20) lower discharge stream, and a non-condensate can be discharged as an upper discharge stream and supplied to the distillation tower (30). Herein, the condensate can include acrylic acid, and, as a by-product, water, a high-boiling-point material and the like, and the non-condensate can include acetaldehyde, water, carbon monoxide, carbon dioxide, a dilution gas and the like.

The cooling tower (20) can be operated under a condition of minimizing the content of acetaldehyde in the lower discharge stream. Specifically, the cooling tower (20) lower discharge stream is transferred to the acrylic acid purification unit for purifying acrylic acid, and there is a problem in that quality and productivity of a product decline by facilitating polymer formation caused by acetaldehyde in the acrylic acid purification process. In regard thereto, the present disclosure minimizes the content of acetaldehyde effused as the cooling tower (20) lower discharge stream by controlling an operation condition of the cooling tower (20). For example, a flow rate of acetaldehyde in the cooling tower (20) lower discharge stream can be 3% or less, from 0.1% to 2.5% or 0.5% to 2% with respect to a flow rate of acetaldehyde in the reactor (10) discharge stream.

In order to minimize the content of acetaldehyde in the cooling tower (20) lower discharge stream, a certain amount of water needs to be included in the cooling tower (20) upper discharge stream. Specifically, when including a certain amount of water in the cooling tower (20) upper discharge stream, acetaldehyde having a lower boiling point than water can be mostly included in the cooling tower (20) upper discharge stream. On the other hand, in order to including most of acetaldehyde without including water in the cooling tower (20) upper discharge stream, the number of levels needs to be increased in the cooling tower (20) to increase separation efficiency, or the type needs to be changed to a distillation tower type by adding a reboiler, which is inefficient. Accordingly, the present disclosure is capable of minimizing the amount of acetaldehyde effused as the cooling tower (20) lower discharge stream using an efficient method of including a certain amount of water in the cooling tower (20) upper discharge stream. For example, a flow rate of water in the cooling tower (20) upper discharge stream can be from 20% to 50%, 30% to 50% or 35% to 50% with respect to a flow rate of water in the reactor (10) discharge stream.

In addition, when operating the cooling tower (20) so as to include a certain amount of water in the cooling tower (20) upper discharge stream, acrylic acid can be effused together as the cooling tower (20) upper discharge stream. For example, a flow rate of acrylic acid in the cooling tower (20) upper discharge stream can be from 5% to 50%, 20% to 50% or 30% to 50% with respect to a flow rate of acrylic acid in the reactor (10) discharge stream. Accordingly, losing an excess amount of acrylic acid has been evitable in the art in order to reduce the content of acetaldehyde in the cooling tower (20) lower portion before transferring the reaction product to the acrylic acid purification unit. In view of the above, the present disclosure additionally installs the distillation tower (30) and supplies the cooling tower (20) upper discharge stream to the distillation tower (30), and acrylic acid effused to the cooling tower (20) upper portion can be recovered.

The operation pressure of the cooling tower (20) can be, for example, from 30 kPa to 1000 kPa, 50 kPa to 500 kPa or 60 kPa to 300 kPa. By operating the cooling tower (20) in the above-mentioned range, the content of acetaldehyde effused to the lower portion can be minimized while including a certain amount of water in the cooling tower (20) upper discharge stream.

A portion of the stream of the cooling tower (20) lower discharge stream is refluxed to the cooling tower (20) after passing through one or more coolers, and the remaining stream can be transferred to the acrylic acid purification unit. For example, a portion of the stream of the cooling tower (20) lower discharge stream can be refluxed to the cooling tower (20) after passing through a first cooler (21) or a first cooler (21) and a second cooler (22). Herein, an operation condition of the first cooler (21), an operation condition of the second cooler (22) and a reflux ratio of the cooling tower (20) lower portion can be properly adjusted depending on the operation condition of the cooling tower (20).

In each of the first cooler (21) and the second cooler (22), one or more types of cooling waters selected from among, for example, cooling water, chilled water and brine can be used as a refrigerant. As a specific example, relatively inexpensive cooling water can be used in the first cooler (21) and the second cooler (22).

The purification unit can include, for example, a step of separating water for removing water included in the cooling tower (20) lower discharge stream and a step of separating the high-boiling-point material, and through this, acrylic acid separated in high purity can be obtained.

According to one embodiment of the present disclosure, a non-condensate not condensed in the cooling tower (20) can be discharged as the cooling tower (20) upper discharge stream and supplied to the distillation tower (30). Herein, the distillation tower (30) can be for separating and recovering acrylic acid included in the cooling tower (20) upper discharge stream.

Specifically, acrylic acid separated in the distillation tower (30) is discharged as the distillation tower (30) lower discharge stream and circulated to the cooling tower (20), and acetaldehyde, carbon monoxide, carbon dioxide, a dilution gas and the like can be discharged as a distillation tower (30) upper discharge stream.

The distillation tower (30) upper discharge stream goes through a condenser (32), and a portion of the stream can be refluxed to the distillation tower (30) and the remaining stream can be discharged. Herein, a reflux ratio of the distillation tower (30) upper portion can be properly adjusted depending on the operation condition of the distillation tower (30).

The distillation tower (30) upper discharge stream can go through an additional purification process as necessary, and by purifying acetaldehyde included in the distillation tower (30) upper discharge stream therethrough and separately selling the acetaldehyde, production costs of acrylic acid can be lowered, and competitiveness can be secured.

The distillation tower (30) lower discharge stream is heated by going through a reboiler (31) before being circulated to the cooling tower (20), and then a portion of the stream can be circulated to the cooling tower (20) and the remaining stream can be refluxed to the distillation tower (30). Herein, a reflux ratio of the distillation tower (30) lower portion can be properly adjusted depending on the operation condition of the distillation tower (30).

In addition, the distillation tower (30) discharge stream is, before being circulated to the cooling tower (20), heat exchanged with some stream of the cooling tower (20) lower discharge stream in one or more coolers installed below the cooling tower (20) without using a separate reboiler (31), and then a portion of the stream is circulated to the cooling tower (20), and the remaining stream can be refluxed to the distillation tower (30). As a specific example, the distillation tower (30) lower discharge stream is, before being circulated to the cooling tower (20), supplied to the first cooler (21) as a refrigerant and heat exchanged by a counter-current flow, a co-current flow or a cross flow with some stream of the cooling tower (20) lower discharge stream, and a portion of the stream is circulated to the cooling tower (20), and the remaining stream can be refluxed to the distillation tower (30). Specifically, acrylic acid discharged to the cooling tower (20) upper portion is included in wastewater and discharged out of the process, or needs to go through a distillation process to be recovered, which can consume additional energy, however, as described above, acrylic acid can be recovered without increasing the amount of process energy used by utilizing heat removed from the cooler below the cooling tower (20) as a heat source required for the reboiler (31) below the distillation tower (30) lower portion as above.

The operation pressure of the distillation tower (30) can be from 10 kPa to 900 kPa, 30 kPa to 600 kPa or 40 kPa to 200 kPa. By operating the distillation tower (30) in the above-mentioned range, as much acrylic acid can be recovered as the distillation tower (30) lower discharge stream and circulated to the cooling tower (20).

A flow rate of acrylic acid in the distillation tower (30) upper discharge stream can be 3% or less, from 0.1% to 3% or 0.1% to 1.5% with respect to a flow rate of acrylic acid in the reactor (10) discharge stream. By recovering as much acrylic acid in the distillation tower (30) as above, loss of acrylic acid can be prevented.

In order to heat exchange the distillation tower (30) lower discharge stream and some stream of the cooling tower (20) lower discharge stream, operation pressures of the distillation tower (30) and the cooling tower (20) can be controlled. For example, the operation pressure of the distillation tower (30) can be controlled to be lower than the operation pressure of the cooling tower (20). As a specific example, the operation pressure of the distillation tower (30) can be controlled to be lower than the operation pressure of the cooling tower (20) by 20 kPa to 900 kPa, 30 kPa to 500 kPa or 50 kPa to 200 kPa. By controlling the operation pressures of the distillation tower (30) and the cooling tower (20) within the above-mentioned range, the distillation tower (30) lower discharge stream and some stream of the cooling tower (20) lower discharge stream can be heat exchanged due to a temperature difference, and through this, acrylic acid can be recovered in the distillation tower (30) without increasing the amount of energy used, and circulated to the cooling tower (20). In addition, the amount of a refrigerant used can be reduced through heat exchange between the distillation tower (30) lower discharge stream and some stream of the cooling tower (20) lower discharge stream.

According to one embodiment of the present disclosure, devices such as a distillation tower, a condenser, a reboiler, a valve, a pump, a separator and a mixer can be further installed as necessary in the method for producing acrylic acid.

Hereinbefore, the method for producing acrylic acid according to the present disclosure has been described and illustrated in the drawings, however, the descriptions and the illustration in the drawings are describing or illustrating only essential components for understanding the present disclosure, and processes and devices not separately described and illustrated other than the processes and the devices described and illustrated in the drawings can be properly applied and used to work the method for producing acrylic acid according to the present disclosure.

Hereinafter, the present disclosure will be described in more detail with reference to examples. However, the following examples are for illustrative purposes only, and it is apparent to those skilled in the art that various changes and modifications can be made within the category and the scope of technical ideas of the present disclosure, and the scope of the present disclosure is not limited thereto.

EXAMPLES

Example 1

For a process flow chart illustrated in FIG. 1, the process for producing acrylic acid was simulated using an Aspen Plus simulator of Aspen Technology Inc.

Specifically, lactic acid and nitrogen ($N_2$) as a dilution gas were supplied to a reactor (10) and went through a dehydration reaction to prepare a reaction product including acrylic acid (AA), and a reactor (10) discharge stream including the reaction product was supplied to a cooling tower (20).

The reactor (10) discharge stream was condensed in the cooling tower (20), and the non-condensate was discharged as an upper discharge stream and supplied to a distillation tower (30). In addition, the condensate was discharged from the cooling tower (20) as a lower discharge stream at a temperature of 117° C., and a portion of the stream was refluxed to the cooling tower (20) after passing through a first cooler (21), and the remaining stream was supplied to an acrylic acid purification unit. Herein, an operation pressure of the cooling tower (20) was controlled at 200 kPa.

In the distillation tower (30), a lower discharge stream of 113° C. including acrylic acid was passed through a reboiler (31), and a portion of the stream was refluxed to the distillation tower (30) and the remaining stream was circulated to the cooling tower (20). In addition, an upper discharge stream including acetaldehyde in the distillation tower (30) was passed through a condenser (32), and a portion of the stream was refluxed to the distillation tower (30) and the remaining stream was discharged. Herein, an operation pressure of the distillation tower (30) was controlled at 190 kPa.

As a result, a flow rate (kg/hr) for each component in each stream is shown in the following Table 1.

TABLE 1

|  | 1-1 | 1-2 | 1-3 | 1-4 | 1-5 |
|---|---|---|---|---|---|
| $N_2$ | 101.2 | 0.0 | 101.2 | 101.2 | 0.0 |
| $CO/CO_2$ | 28.7 | 0.0 | 28.6 | 28.7 | 0.0 |
| ACHO | 14.0 | 0.2 | 13.7 | 13.8 | 0.1 |

TABLE 1-continued

|  | 1-1 | 1-2 | 1-3 | 1-4 | 1-5 |
|---|---|---|---|---|---|
| $H_2O$ | 597.2 | 538.0 | 59.3 | 244.9 | 185.6 |
| AA | 240.5 | 238.0 | 2.5 | 56.6 | 54.1 |
| High-Boiling-Point Material | 18.5 | 16.6 | 1.9 | 5.8 | 3.9 |
| Total | 1000.1 | 792.8 | 207.2 | 451.0 | 243.7 |

The total is a value obtained by rounding off the value obtained in the Aspen Plus simulator to the nearest tenth.

When referring to Table 1, it was identified that, in Example 1, the amount of acetaldehyde in the cooling tower (20) lower discharge stream transferred to the purification unit was very small of approximately 1.4% of acetaldehyde included in the reaction product, and it was identified that loss of acrylic acid was very small with the amount of acrylic acid effused as the distillation tower (30) upper discharge stream being approximately 1% of acrylic acid included in the reaction product.

Example 2

For a process flow chart illustrated in FIG. 2, the process for producing acrylic acid was simulated using an Aspen Plus simulator of Aspen Technology Inc.

Specifically, lactic acid and nitrogen ($N_2$) as a dilution gas were supplied to a reactor (10) and went through a dehydration reaction to prepare a reaction product including acrylic acid (AA), and a reactor (10) discharge stream including the reaction product was supplied to a cooling tower (20).

The reactor (10) discharge stream was condensed in the cooling tower (20), and the non-condensate was discharged as an upper discharge stream and supplied to a distillation tower (30). In addition, the condensate was discharged from the cooling tower (20) as a lower discharge stream at a temperature of 117° C., and a portion of the stream was refluxed to the cooling tower (20) after passing through a first cooler (21) and a second cooler (22), and the remaining stream was supplied to an acrylic acid purification unit. Herein, an operation pressure of the cooling tower (20) was controlled at 200 kPa.

In the distillation tower (30), a lower discharge stream of 96° C. including acrylic acid was supplied to the first cooler (21) and heat exchanged with a portion of the stream of the cooling tower (20) lower discharge stream, and a portion of the stream was refluxed to the distillation tower (30), and the remaining stream was circulated to the cooling tower (20). In addition, an upper discharge stream including acetaldehyde in the distillation tower (30) was passed through a condenser (32), and a portion of the stream was refluxed to the distillation tower (30) and the remaining stream was discharged. Herein, an operation pressure of the distillation tower (30) was controlled at 110 kPa.

As a result, a flow rate (kg/hr) for each component in each stream is shown in the following Table 2.

TABLE 2

|  | 2-1 | 2-2 | 2-3 | 2-4 | 2-5 |
|---|---|---|---|---|---|
| $N_2$ | 101.2 | 0.0 | 101.2 | 101.2 | 0.0 |
| $CO/CO_2$ | 28.7 | 0.0 | 28.6 | 28.7 | 0.0 |
| ACHO | 14.0 | 0.2 | 13.7 | 13.9 | 0.1 |
| $H_2O$ | 597.2 | 537.7 | 59.5 | 238.6 | 179.1 |

TABLE 2-continued

|  | 2-1 | 2-2 | 2-3 | 2-4 | 2-5 |
|---|---|---|---|---|---|
| AA | 240.5 | 238.0 | 2.5 | 55.1 | 52.6 |
| High-Boiling-Point Material | 18.5 | 16.8 | 1.6 | 5.8 | 4.1 |
| Total | 1000.1 | 792.7 | 207.1 | 443.3 | 235.9 |

When referring to Table 2, it was identified that, as in Example 1, loss of acrylic acid was very small while reducing the amount of acetaldehyde in the cooling tower (20) lower discharge stream transferred to the purification unit in Example 2 as well.

In addition thereto, acrylic acid discharged to the cooling tower (20) upper portion was able to be recovered without using additional energy by heat exchanging the distillation tower (30) lower discharge stream and a portion of the stream of the cooling tower (20) lower discharge stream in the first cooler (21), and thereby using, as a calorie (amount of heat) to be supplied to the reboiler (31) in Example 1, a calorie of approximately 33233 kcal/hr removed from the first cooler (21).

COMPARATIVE EXAMPLE

Comparative Example 1

For a process flow chart illustrated in FIG. 3, the process for producing acrylic acid was simulated using an Aspen Plus simulator of Aspen Technology Inc.

Specifically, lactic acid and nitrogen as a dilution gas were supplied to a reactor (10) and went through a dehydration reaction to prepare a reaction product including acrylic acid (AA), and a reactor (10) discharge stream including the reaction product was supplied to a cooling tower (20).

The reactor (10) discharge stream was condensed in the cooling tower (20), the non-condensate was discharged as an upper discharge stream, the condensate in the cooling tower (20) was discharged as a lower discharge stream, and a portion of the stream was refluxed to the cooling tower (20) after passing through a first cooler (21), and the remaining stream was supplied to an acrylic acid purification unit. Herein, an operation pressure of the cooling tower (20) was controlled at 200 kPa, and by controlling the circulation flow rate at which the lower discharge stream of the cooling tower (20) is circulated to the cooling tower (20) after going through the first cooler (21), the amount of acetaldehyde effused as the cooling tower (20) lower discharge stream was minimized.

As a result, a flow rate for each component in each stream is shown in the following Table 3.

TABLE 3

|  | 3-1 | 3-2 | 3-3 |
|---|---|---|---|
| $N_2$ | 101.2 | 0.0 | 101.2 |
| $CO/CO_2$ | 28.7 | 0.0 | 28.6 |
| ACHO | 14.0 | 0.2 | 13.7 |
| $H_2O$ | 597.2 | 537.7 | 59.5 |
| AA | 240.5 | 227.6 | 12.9 |
| High-Boiling-Point Material | 18.5 | 17.1 | 1.4 |
| Total | 1000.1 | 782.6 | 217.3 |

Comparative Example 2

An operation was conducted in the same manner as in Comparative Example 1 except for increasing the circulation flow rate at which the lower discharge stream of the cooling tower (20) is circulated to the cooling tower (20) after going through the first cooler (21).

As a result, a flow rate for each component in each stream is shown in the following Table 4.

TABLE 4

|  | 3-1 | 3-2 | 3-3 |
| --- | --- | --- | --- |
| $N_2$ | 101.2 | 0.0 | 101.2 |
| $CO/CO_2$ | 28.7 | 0.0 | 28.6 |
| ACHO | 14.0 | 1.6 | 12.3 |
| $H_2O$ | 597.2 | 592.7 | 4.5 |
| AA | 240.5 | 239.7 | 0.8 |
| High-Boiling-Point Material | 18.5 | 18.4 | 0.1 |
| Total | 1000.1 | 852.4 | 147.5 |

When referring to Table 3 and Table 4, the circulation flow rate at which the lower discharge stream of the cooling tower (20) is circulated to the cooling tower (20) after going through the first cooler (21) was adjusted in Comparative Example 1 to minimize the amount of acetaldehyde in the cooling tower (20) lower discharge stream as in the examples, and it was identified that the amount of acrylic acid effused as the cooling tower (20) upper discharge stream was very high of approximately 5.4% of acrylic acid included in the reaction product.

In addition, in Comparative Example 2, it was identified that, when the amount of acrylic acid effused as the cooling tower (20) upper discharge stream was minimized compared to in Comparative Example 1, the amount of acetaldehyde in the cooling tower (20) lower discharge stream was very high of approximately 12% of acetaldehyde included in the reaction product.

The invention claimed is:

1. A method for producing acrylic acid, the method comprising the following steps in sequence:

preparing a reaction product including acrylic acid by supplying lactic acid to a reactor and performing a dehydration reaction;

supplying a reactor discharge stream including the reaction product to a cooling tower that condenses through cooling the reactor discharge stream in a gas phase to yield a condensate and a non-condensate and transferring a lower discharge stream including the condensate to an acrylic acid purification unit, and supplying the non-condensate discharged as an upper discharge stream to a distillation tower; and in the distillation tower, circulating a distillation tower lower discharge stream including acrylic acid to the cooling tower, and removing acetaldehyde from a distillation tower upper discharge stream, wherein the cooling tower has an operation pressure of 200 kPa to 1000 kPa, and the distillation tower has an operation pressure of 100 kPa to 900 kPa, and wherein the operation pressure of the distillation tower is lower than the operation pressure of the cooling tower, wherein a partial stream of the cooling tower lower discharge stream is refluxed to the cooling tower after passing through a first cooler, wherein the distillation tower lower discharge stream is heated by going through a reboiler before being circulated to the cooling tower, and then a partial stream is circulated to the cooling tower and the remaining stream is refluxed to the distillation tower, and the heat source of the reboiler uses the heat removed from the first cooler.

2. The method of claim 1, wherein a partial stream of the cooling tower lower discharge stream passing through the first cooler further passes through a second cooler, and refluxed to the cooling tower.

3. The method of claim 1, wherein the distillation tower lower discharge stream is, before being circulated to the cooling tower, supplied to the first cooler and heat exchanged with a partial stream of the cooling tower lower discharge stream, and a partial stream of the heat exchanged stream is circulated to the cooling tower and the remaining stream is refluxed to the distillation tower.

4. The method of claim 1, wherein the operation pressure of the distillation tower is lower than the operation pressure of the cooling tower by 20 kPa to 900 kPa.

5. The method of claim 1, wherein a flow rate of acetaldehyde in the cooling tower lower discharge stream is 3% or less with respect to a flow rate of acetaldehyde in the reactor discharge stream.

6. The method of claim 1, wherein a flow rate of acrylic acid in the distillation tower upper discharge stream is 3% or less with respect to a flow rate of acrylic acid in the reactor discharge stream.

* * * * *